United States Patent [19]

Ojo-Amaize et al.

[11] Patent Number: 5,801,193
[45] Date of Patent: Sep. 1, 1998

[54] COMPOSITIONS AND METHODS FOR IMMUNOSUPPRESSING

[75] Inventors: Emmanuel A. Ojo-Amaize, Glendora, Calif.; Joseph L Okogun, New Rochelle, N.Y.; Howard B. Cottam, Fallbrook, Calif.

[73] Assignee: Immune Modulation, Inc., Santa Monica, Calif.

[21] Appl. No.: 843,401

[22] Filed: Apr. 15, 1997

[51] Int. Cl.$^6$ .............. A61K 31/335; A61K 31/535; C07D 413/00; C07D 303/36
[52] U.S. Cl. .............. 514/475; 514/232.8; 544/147; 549/551; 549/554
[58] Field of Search .............. 544/147; 549/551; 549/554; 514/232.8, 475

[56] References Cited

U.S. PATENT DOCUMENTS 5,338,758  8/1994  Chu et al. .............. 514/468
5,407,816  4/1995  Bringi et al. .............. 435/123

*Primary Examiner*—Raymond Henley, III
*Attorney, Agent, or Firm*—Harris F. Brotman

[57] ABSTRACT

Methods and compounds for inducing immunosuppression in animals which need immunosuppressive treatment involving administration to animals of a therapeutically effective amount of a compound of the following formula

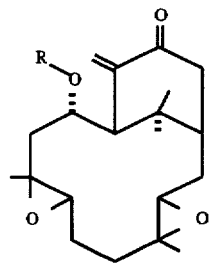

where R is H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_nCOOR_2$ where n=1–4 where $R_2$ is H, an alkalai metal salt, an alkaline earth metal salt, $NH_4^+$, $N^+(R_3)_4$ where $R_3$ is independently selected from the group consisting of H and alkyl of 1 to 4 carbon atoms, $COR_1$ wherein $R_1$ is selected from the group consisting of H, $(CH_2)_nCH_3$, where n=1–6, $(CH_2)_nCOOR_2$ where n=1–4 and $R_2$ is previously defined, $(CH_2)_nN^+(R_3)_4$ wherein n=1–4, and $(CH_2)_nSO_3^-$ where N=1–4, and pharmaceutically acceptable salts thereof.

4 Claims, 8 Drawing Sheets

Effect of JO-4A on NK-activity in B6 mice

COMPOSITIONS AND METHODS FOR IMMUNOSUPPRESSING

BACKGROUND OF THE INVENTION

1. Field of the Invention

This invention relates to immunosuppressive agents and their use in transplantation therapy. In particular, the invention is directed to the use of diterpene compounds, in particular hypoestoxides, derivatives and agonists thereof for immunosuppressing inflammation, graft rejection, graft-versus-host-disease (GVHD), skin diseases, and T-cell-mediated autoimmune diseases such as arthritis, systemic lupus erythematosus, thyroiditis, multiple sclerosis, glomerulonephritis, diabetes, and allergy.

2. Background Art

Many human diseases are characterized by excessive or inappropriate immune responses. In transplantation, the immune system attacks major histocompatibility complex (MHC)-disparate donor tissue leading to graft rejection. In allergy or inflammation, the immune system is hyperresponsive to otherwise harmless environmental antigens. In autoimmune diseases, the immune system attacks normal self-tissues. In immunodeficiency diseases such as HIV infection and AIDS, an infectious agent attacks the host's immune system. It is now recognized that immunosuppressive therapy is appropriate for treating each of these disorders (Blood Reviews 1995;9:117–133). The development of naturally occurring secondary metabolites of cyclosporin A (CsA), FK506 and rapamycin as immunosuppressants has revolutionized organ transplantation through their use in the prevention of graft rejection (TIBS 1993;18:334–338) and GVHD (Ann Hematol 1995;71:301–306). There are, however, serious side effects associated with use of these drugs, such as nephrotoxicity, neurotoxicity, hepatotoxicity, endocrine complications and bone effects (New Engl J Med (1989)321:1725–1738; Kahan BD et al. Surgery (1985) 97:125). There is, therefore, a clinical need to provide new compounds for effective immunosuppression without these side effects.

DISCLOSURE OF THE INVENTION

Applicants' invention rests on their finding that a select group of hypoesxtoxide analogs possess unexpected effectiveness as immunosuppressive agents.

Accordingly, one aspect of the invention is directed to compounds of the formula

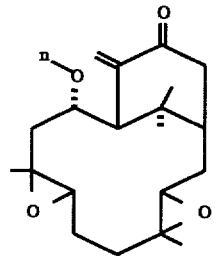

I where:

R is (i) H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_nCOOR_2$ where n=1–4 where $R_2$ is H, an alkalai metal salt, an alkaline earth metal salt, $NH_4^+$, $N^+(R_3)_4$ where $R_3$ is independently selected from the group consisting of H and alkyl of 1 to 4 carbon atoms, or (ii) $COR_1$ wherein $R_1$ is selected from the group consisting of H, $(CH_2)_nCH_3$, where n=1–6, $(CH_2)_nCOOR_2$ where n=1–4 and $R_2$ is previously defined, $(CH_2)_nN^+(R_3)_4$ wherein n=1–4, and $(CH_2)_nSO_3^-$ where n=1–4, and pharmaceutically acceptable salts thereof.

A related aspect is directed to pharmaceutical compositions comprising a therapeutically effective immunosuppressant amount of the compounds of formula I.

Another aspect of the invention is directed to methods for inducing immunosuppression in animals which need immunosuppressive treatment. The method comprises administering to animals pharmaceutical compositions comprising a therapeutically effective immunosuppresant amount of hypoestoxide (herein designated JO-4 and illustrated in formula IV) or one or more of the compounds of formula I.

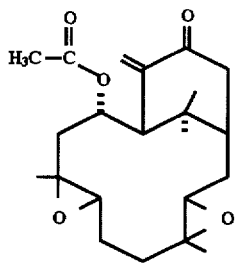

IV

MODES OF CARRYING OUT THE INVENTION

General Description and Definitions

Figure 1:
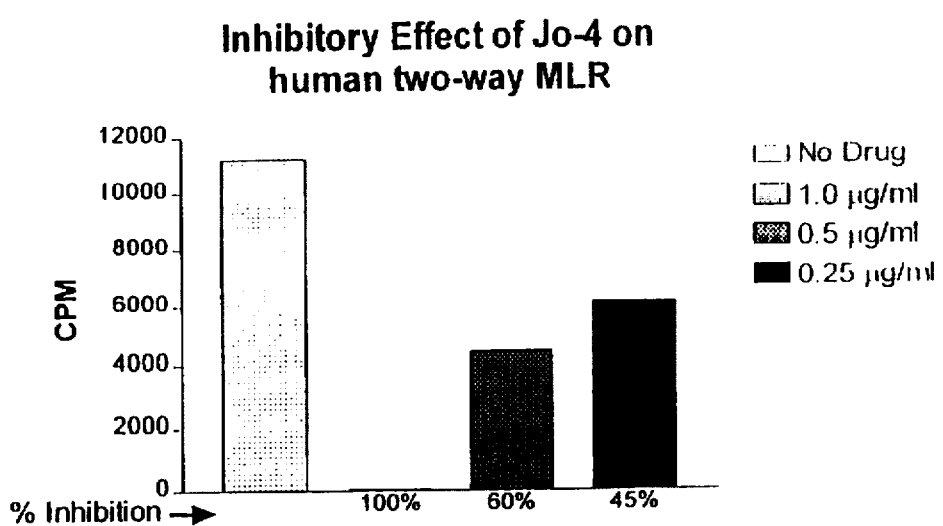
FIG. 1 shows the inhibitory effects of JO-4 on a human two-way mixed lymphocyte reaction. PBMCs from two individuals were co-cultured in the presence of varying concentrations of JO-4 for 5 days. Proliferation was measured by $^3$H-thymidine incorporation and expressed as CPM and % inhibition of controls wells without JO-4.

The practice of the present invention will employ, unless otherwise indicated, conventional molecular and cellular immunology, cell biology, biochemistry, and organic and medicinal chemical synthesis within the skill of the art. Such techniques are explained fully in the literature. See, e.g. Abbas, A. K., et al., eds, 1994, 2nd ed. Cellular and Molecular Immunology, W. B. Saunders Co., USA; Harlow, E. and D. Lane, Antibodies, A Laboratory Manual, Cold Spring Harbor Laboratory, 1988; Auchincloss, Jr., H. and Sachs, D. H. Transplantation and Graft Rejection in: Fundamental Immunology, Paul, W. E. ed., 1993, Raven Press; Silverman, Richard B., The Organic Chemistry of Drug Design and Drug Action, Academic Press, Inc. NY (1992); Smith, Michael B., Organic Synthesis, McGraw Hill, Inc., NY, (1994)).

The following terminology will be used in accordance with the definitions set out below in describing the present invention.

For purposes of the invention, the term "immunosuppressive treatment" refers to an approach to the prevention and management of diseases and syndromes, which require for therapy the suppression of lymphocytes and immunocytes. Such diseases and syndromes include, but are not limited to, graft vs. host disease (GVH), autoimmune diseases such as diabetes, rheumatoid arthritis, systemic lupus erythematosus, thyroiditis, multiple sclerosis, glomerulonephritis, and allergy. It is understood that a commonly used method of immunosuppression involves administering to an animal in need of such treatment a therapeutically effective amount of an immunosuppressive agent (e.g. cyclosporin A, FK506, or the compositions and methods exemplifed and claimed herein) in order to inhibit T-cell activity or Tcell response.

The terms "lymphocytes and immunocytes" refer to cells that mediate the specificity of immune responses. As used herein, the terms refer to T lymphocytes, which are described in detail in Abbas et al.

"Natural killer cells" or "NK cells" are non-T, non-B lymphocytes usually having granular morphology. NK cells are important in innate immunity to viruses and other intracellular pathogens as well as in antibody-dependent cell-mediated cytotoxicity (ADCC). NK cells are responsible in large degree for graft versus host disease (GVHD) (Ferrara, J. L. M., et al. (1989) Transplantation 47:50–54; Ghayur, T. et al. (1987) Transplantation 44:261–267; Ghayur, T., et al. (1988) Transplantation 45:586–590. As demonstrated in the Examples below, it was found that the compounds and methods of the invention suppressed NK cell activity in vivo and found use in preventing or overcoming GVHD in animals in need of such treatment.

The term "transplantation" refers to the process of taking cells, tissues, or organs, called a graft, from one individual and, usually, placing them into a different, genetically non-identical recipient. The individual who provides the graft is referred to as the donor, and the individual who receives the graft is referred to as either the recipient or host. Transplantation leads to a specific immune response, called rejection, that can destroy the graft. Transplant tissues include solid organs, such as liver, heart, and kidneys; and other tissues such as skin and bone marrow. In vivo rejection is mediated by T cells. Rejection may be prevented or treated by immunosuppressing the recipient (host) by administering to the host therapeutically effective amounts of compounds such as cyclosporin A or FK506, as well as administering the compositions exemplifed herein. Most immunosuppression is directed at T-cell responses using specific immunosuppressive agents, not unlike the compositions of the present invention. In addition, immunosuppression of NK cell function in donors plays an important therapeutic role in treating conditions such as graft versus host disease (GVHD). Accordingly, transplant donors require preparatory immunosuppression by administration of a therapeutically effective amount of an immunosuppressive agent prior to donating a transplant for prevention of graft versus host disease in a recipient.

The term "animals" is taken to mean humans as well as other animals.

As used herein, the term "JO-4" means a compound which is a bicycle [9,3,1] pentadecane diterpene compound, as described in Z. Naturforsc 37 c: 558–561 (1982) and in Heterocycles 20:2125–2128 (1983), in which reference this compound is named "hypoestoxide." The chemical structure of JO-4 is illustrated in formula IV.

It is understood that the compounds illustrated in formula I include prodrugs of JO4A. In terms of formula I, JO-4A is derived from JO-4 when R is H. The struture of JO-4A is illustrated in formula III.

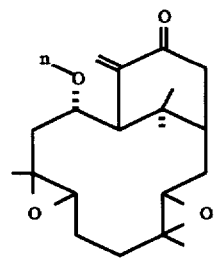

III

The term "prodrug," as used herein, refers to a pharmacologically inactive compound that is converted to an active drug by a metabolic transformation. (Silverman, Richard B. The Organic Chemistry of Drug Design, Acad. Press, 1992). There are numerous reasons why a prodrug strategy is used in drug design, the most common of which are to overcome problems associated with the compound, such as solubility, absorption and distribution, site specficity, instability, prolonged release, toxicity, poor patient acceptability, and formulation. Literature is available for guidance without undue experimentation for determining how to get compounds in pharmaceutical compositions to a locus to permit them to act, and guidance for how to obtain an immunosuppressive therapeutic effective amount at the locus of action (Harnden, M. R. et al., J. Med. Chem. 32:1738–1743 (1989); Lake-Bakaar, D. M., et al, Antimicrobial Agents and Chemotherapy 33:110–112 (1989); Baker, D. C., et al. J. Medicinal Chemistry 21:1218–1221 (1978); Hussain, M. A. et al., J. Pharmaceutical Sciences, 76:356–358 (1987); Varia, S. A. et al., J. Pharmaceutical Sciences 73:1068–1073 (1984)).

The most common prodrug form for drugs containing alcohol or carboxylic acid functional groups is an ester. Using skills well known in the art, it is possible to alter the structure of the compound to improve its pharmacokinetic properties and, thereby, transform it into a useful drug for therapeutic administration to an animal or human. Accordingly, the rationale for medicinal activity (i.e. inducing immunosuppression) of the claimed prodrugs of JO-4A is that JO-4 itself, the natural product, is a potent immunosuppressive agent. JO-4 is also a prodrug for JO-4A in the presence of serum esterases in the in vivo setting, and, in the in vitro setting if the culture medium contains added serum (which is most often the case). A preferred embodiment of the immunosuppressant agent is the metabolite JO-4A, which is the free alcohol derivative of JO-4. JO-4 serves as an ester prodrug form for the delivery of JO-4A, which is formed over time after administration of JO-4 to cells or animals. In similar fashion, many other ester prodrugs of JO-4A provide delivery of JO-4A. Such prodrug forms and methods for making them are well known in the art, as cited above. These prodrugs are known to yield the parent drugs of interest upon exposure to esterases commonly found in serum of animals and humans. It is understood that the prodrugs of JO-4A claimed herein yield JO-4A and are as active or more active in terms of inducing immunosuppression than the natural product JO-4.

The term "agonists" as used herein refers to substances that elicit the same response (i.e. inducing immunosuppression in animals in need of such treatment) as the compounds indicated in formula I. Agonists of the compounds of formula I include, but are not restricted to the prodrugs of JO-4A, which prodrugs are illustrated in formula I.

Methods for determining or screening modified forms of the claimed compounds, i.e. prodrugs and/or agonists of the claimed compounds, for their ability to induce immunosuppression in animals in animals in need of such treatment are well known in the art.

The methods of the present invention are directed to immunosuppressive therapy using the compounds of formula I, as well as the compounds of formula IV (JO-4, i.e. hypoestoxide). In particular, the methods of the present invention involve administering to an animal in need of such treatment a therapeutically effective amount of the compounds of formulas I or IV. An embodiment of the methods involves associating compounds of formulas I or IV with a pharmaceutical carrier or diluent for administration to an animal. The method of the invention finds use in suppressing the rejection of transplants in animals, as illustrated by the effects of JO-4 or JO-4A on cellular immunity in the one-way and two-way MLR tests set forth below. Thus, the method of the invention is useful in the suppression of the formation of, or proliferation of immunocytes or lymphocytes, and is therefore useful in the treatment of autoimmune diseases, and in suppressing the rejection of transplants, e.g. organ transplants, such as skin, bone marrow, kidney, liver and heart transplants. The effects of JO-4 or JO-4A were ascertained in the tests described below.

As indicated by FIGS. 1–8, compounds and the method of the invention find use in treating autoimmune diseases in animals. It is understood that immunosuppressants for T-cells, such as cyclosporin A (Forsell, T et al., J. Urol, 1996, 5:1591–3; Yocum, D. E., et al., Rheum. Dis. Clin. North. Am., 1995, 3: 835–44) or tacrolimus (Ketel, B. L., et al., Transplant. Proc., 1996, 2:899) suppresses immune reactions and result in inhibition or amelioration of autoimmune disorders. T-cells and their products (cytokines) are known to be involved in the generation and production of autoimmune reactions in vivo.

For all of the above-mentioned uses, the therapeutic effective amount or dosage will, of course, vary depending on the compound employed, mode of administration and treatment desired. However, in general, satisfactory results would be obtained when administered orally at a daily dosage of from about 1 mg to about 600 mg per kg animal body weight, conveniently given in divided doses 1 to 4 times a day or in sustained release form. If administered by injection, in general, satisfactory results would be obtained when administered at a daily dosage of from about 1 mg to about 200 mg per kg animal body weight, conveniently given in divided doses 1 to 4 times a day or in sustained release form. For the larger mammals, the total daily dosage would be in the range of from about 5 to about 500 mg, and dosage forms suitable for oral administration comprise from about 5 mg to about 500 mg of the compounds admixed or in association with a solid or liquid pharmaceutical carrier or diluent. Methods are well known in the art for determining therapeutically effective amounts of the compounds of the invention. Such methods involve analysis of the pharmaceutical/pharmacokinetic parameters in immunosuppressive therapy for inducing immunosuppression, for suppressing formation of lymphocytes and immunocytes, for treating autoimmune diseases, and for suppressing rejection of transplants in animals or other indications ( Recent Developments in Transplantation Medicine, Vol. 1: New Immunosuppressive Drugs: eds. D. Przepiorka and H. Sollinger, Physicians and Scientists Pub. Co., Glenview, Ill., 1994).

The method of the present invention includes administering a pharmaceutical composition comprising an effective amount of the compounds of the formulas I, II or IV in pure form or as a pharmaceutically acceptable crude concentrate in association with a pharmaceutical carrier or diluent. Such compositions conveniently contain more than 1% by weight of the compounds of formulas I, II or IV and may be prepared by conventional techniques to be in conventional forms, for example, capsules, tablets, suppositories, dispersible powders, syrups, elixirs, suspensions or solutions for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period. Other compounds and methods known in the art for delaying disintegration or for timed-delayed or time-measured delivery of the active ingredients also find use in formulating the active ingredients for use in the methods of the invention. For example, the compounds of formulas I, II or IV may also be combined with liposomes or other delayed-release carrier means to protect the compounds from degradation until they reach their targets and/or facilitate movement of the compounds across tissue barriers.

The preferred compositions from the standpoint of ease of administration are solid compositions, particularly solid-filled gelatin capsules or tablets.

It is also to be understood that a further embodiment of the method of the invention involves combining one or more agents in a variety of protocols, including prophylaxis, with the method of the invention for administering to animals in need of immunosuppressive treatment pharmaceutical compositions comprising compounds of formulas I, II or IV. Combination protocols and methods for determining their efficacy, including therapeutic drug monitoring, are well known in the art (Lazarus, H. M. et al. Blood Reviews, 1995, 9:117–133; Aggarwal, B. B., et al., eds., 1995, Human Cytokines: Their role in Disease and Therapy, Blackwell Science, Inc., Cambridge, Mass.; Ambrus, J. L. et al., 1993, Surgery, Gynecology & Obstetrics, 176:588). Examples of immunosuppressive agents or agents useful in immunosuppressive therapy which may be combined with administering the compounds of formulas I, II or IV in the method of the invention include, but are not limited to corticosteroids, methotrexate, cyclosporin, rapamycin, FK506 (Prograf™), antithymocyte globulin, monoclonal antibody preparations, polyclonal antibody preparations, interleukin 1 antagonists, interleukin 2 antagonists, TNF antagonists, immunotoxins, thalidomide, interferon, nitric oxide, mizoribine, deoxyspergualin, leflunomide, and anti-adhesion molecules.

It will be further understood that the present invention includes a pharmaceutical composition comprising a therapeutically effective amount of one or more compounds of formulas I, II or IV in association with one or more agents selected from the group of immunosuppressive agents or agents useful in immunosuppressive therapy consisting of corticosteroids, methotrexate, cyclosporin, rapamycin, FK506 (Prograf™), antithymocyte globulin, monoclonal antibody preparations, polyclonal antibody preparations, interleukin 1 antagonists, interleukin 2 antagonists, TNF antagonists, immunotoxins, thalidomide, interferon, nitric oxide, mizoribine, deoxyspergualin, leflunomide, and anti-adhesion molecules. Methods are well known in the art for determining therapeutically effective amounts of the compounds of formulas I, II or IV, and agents selected from the group of immunosuppressive agents or agents useful in immuosuppressive therapy in association with the compounds of formulas I, II or IV in pharmaceutical compositions of the invention ((Lazarus, H. M. et al. Blood Reviews, 1995, 9:117–133; Aggarwal, B. B., et al., eds., 1995, Human Cytokines: Their role in Disease and Therapy, Blackwell Science, Inc., Cambridge, Mass.; Ambrus, J. L. et al., 1993, Surgery, Gynecology & Obstetrics, 176:588).

The following materials and methods were employed in the non-limiting Examples set out below.

Blood donors: Heparinized blood (30 cc) was obtained by venipuncture from volunteers. Two donors of different genetic backgrounds are usually required to initiate a mixed leukocyte culture (MLC).

Culture medium: RPMI-1640 medium (Fisher Scientific Co., Santa Clara, Calif.) was supplemented with 20% heat-inactivated human AB serum and 1% penicillin/streptomycin mixture.

Isolation of mononuclear leukocytes: Mononuclear leukocytes were isolated from the blood by layering appropriate diluted blood in Hanks-balanced salt solution (H-BSS) on ficoll-hypaque gradient followed by centrifugation. The recovered cells were washed three times in culture medium, and viability was determined by trypan blue dye exclusion method. Cell concentration was adjusted to $2 \times 10^6$/ml in complete culture medium.

Mixed leukocyte reaction (MLR)

The MLR is an assay recognized by those skilled in the art as an in vitro predictor of in vivo immunosuppressant activity. The MLR is an in vitro model of T-cell recognition of foreign major histocompatibility complex (MHC) gene products and was used as a predictive test of cell-mediated graft rejection (Abbas, A. K., et al., eds, 1994, 2nd ed. Cellular and Molecular Immunology, W. B. Saunders Co., USA). Graft rejection is carried out by T cells that recognize MHC molecules and destroy the graft. This process can be studied in vivo, but in-depth analysis, especially in humans, required the development of tests such as the MLR as an in vitro correlate of graft rejection. (Janeway, Chas. and Travers, Paul, Immunobiology, 2nd Ed., Garland Publishing, Inc, New York (1996)). It is well known in the art that the MLR is induced by co-culturing mononuclear leukocytes from one individual with mononuclear leukocytes derived from another individual. If there are differences in the alleles of the MHC genes between the two individuals, a large proportion of the mononuclear cells will proliferate over a period of 4–7 days, and is referred to as allogeneic MLR. The level of proliferative response is measured by incorporation of $^3$H-thymidine into DNA during cell replication. Because the cells from each donor react and proliferate against the other, the resultant response is known as a "two-way MLR". JO-4 was tested in the MLR for its ability to "immunosuppress".

"Two-way MLR" set up in microtiter plates

Mononuclear cells (at $2 \times 10^6$/ml) of each donor were first mixed thoroughly together in a 50 ml tube at a 1:1 ratio with volume. The mixture was dispensed into wells of a 96-well U-bottom microtiter plate in volumes of 100 µl per well. Compounds or suspected immunosuppressive agents were added in culture medium in volumes of 100 µl per well at varying concentrations of 1.0, 0.5, or 0.25 µg/ml µM, respectively. 100 µl of culture medium was added to control wells without drug. Cultures were maintained in a humid incubator at 37° C. in an atmosphere of 5% $CO_2$ for 5 days. At 4 hours before harvest, the cultures in each well were pulsed with 1 µCi of tritiated thymidine (specific activity 719.5 mCi/mg; Dupont, Wilmington, Del.). Cells were harvested onto glass fiber filters (Packard, Downers Grove, Ill.) with a 96-well automatic cell harvester (TOMTEC, Hamden, Conn.) and were counted directly on a Matrix 9600 beta counter (Packard). The results are shown in FIG. 1.

Data were expressed as percent inhibition (% Inhibition) according to the following formula:

$$\% \text{ Inhibition} = 100 - \left( \frac{\text{Counts per minute } (CPM) \text{ for wells with drug}}{CPM \text{ for wells without drug}} \times 100 \right)$$

Figure 2:
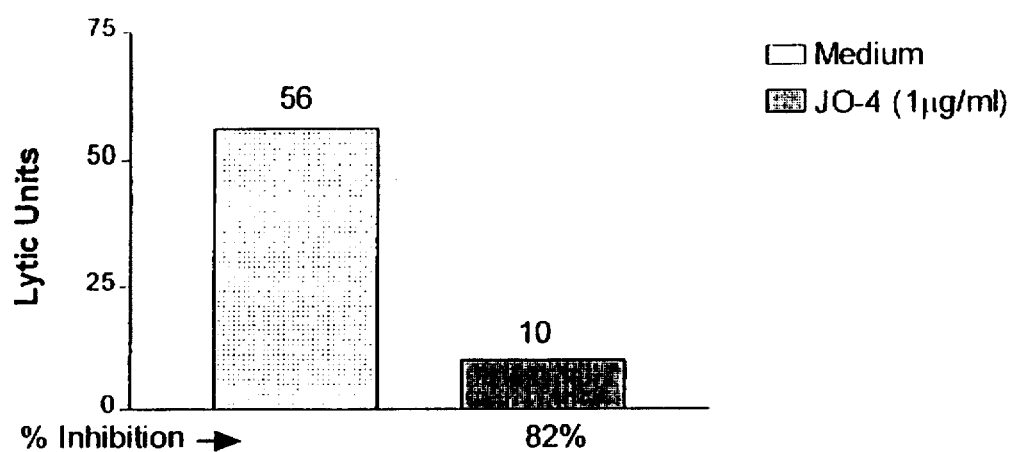
FIG. 2 shows the inhibitory effect of JO-4 on one-way MLR-generated human T-lymphocyte-mediated cytolysis. Cytotoxic T lymphocytes (CTLs) were generated from one-way MLR in the absence or presence of JO-4 for 5–7 days. At the end of culture, CTLs were harvested and tested in a four hour $^{51}$Cr-release assay against activated lymphocytes which were used as stimulators in the one-way MLR. Results are expressed in lytic units (LU) and as % inhibition.

Generation of MHC-restricted Cytolytic CD8+T-lymphocytes in "One-way Human MLR" Cultures The "one-way MLR" was set up in tissue culture flasks with mononuclear cells from two different donors as in the "two-way MLR" described above. However, in "one-way MLR", one of the two mononuclear leukocyte populations was rendered incapable of proliferation by treatment with mitomycin C, an antimitotic drug, prior to culture. In this "one-way MLR", the treated cells served exclusively as stimulators and the untreated cells, still capable of proliferation, served as the responders. The responder cells, during a 5–7 day culture period, expressed the CD8+ phenotype but not the CD4+. These CD8+ cells served exclusively as cytolytic T lymphocytes (CTLs) which lyse target cells from the same individual as the original stimulator cell population. In transplantation, these MHC-restricted cytotoxic CD8+ T-cells lyse MHC disparate donor tissue targets, leading to graft rejection (Abbas, A. K., eds., 1994, 2nd ed., Cellular and Molecular Immunology, W. B. Saunders Co., USA; Imagawa, D. K., et al., in Aggarwal, B. B., et al., eds., 1995, Human Cytokines: Their role in Disease and Therapy, Blackwell Science, Inc., Cambridge, Mass.). The results are shown in FIG. 2.

"One-way" MLR Set up in Tissue Culture Flasks

Mononuclear cells of one donor were first treated with mitomycin C (Sigma Chem. Co., St. Louis, Mo.) (50 µg/50× $10^6$ cells) in 15 mL tubes wrapped in aluminum foil and incubated in a 37° C. water bath for 1 hr. At the end of incubation, cells were washed 3 times with tissue culture medium and adjusted to $2×10^6$/mL and served as stimulators. Mononuclear cells from another donor which have not been treated with mitomyicin C adjusted to $2×10^6$/mL and used as responders. Responders and stimulators were mixed at a 1:1 ratio with volume and incubated in tissue culture flasks for 5–7 days in the presence of either 1.0 µg/mL JO-4 or medium only. Some of the stimulator cells which were not mitomycin C-treated were activated with PHA and followed by culture in IL-2-conditioned media for use as targets at the end of 5 or 7 days in the CTL assay.

Inhibitory Effects of JO-4A on Natural killer (NK) Cell Activity—Cytotoxicity Assay Mice were treated intravenously or orally with varying doses of JO-4A for varying periods of time. At the end of the treatment period, spleens were removed to test for splenic NK activity against YAC-1 tumor cells, a mouse NK-susceptible cell line (Ojo-Amaize, E. et al., Scand. J. Immunol. (1978) 7:297–306). A 4-hour -$^{51}$Cr-release assay was used as described for the ex vivo mouse CTL assay. Results were expressed as % lysis/LU and as % inhibition of lysis (Ojo-Amaize, E. et al. (1994) Clin. Infectious Diseases 18(Suppl 1):S157–9).

CTL Assay

At the end of the culture period, target cells were labeled with $^{51}$Na$_2$CrO$_4$ ($^{51}$Cr) and adjusted to $0.5×10^6$/mL. Effector cells (i.e., responder cells) were harvested, washed twice in medium and live cells were adjusted to $2.5×10^6$/mL. Effector and target cells were mixed at an effector:target (E:T) cell ratio of 25:1 in 96-well U-bottom microtiter plates and incubated for 4 hr. In a 37° C./5% $CO_2$ incubator. At the end of incubation, lysis of target cells was assessed essentially as described previously for a $^{51}$-Cr-release assay (Ojo-Amaize, E. A., et al., 1994, Clin. Infect. Dis. 18 (Suppl.): S154–159) and results expressed as % specific lysis.

Figure 3:
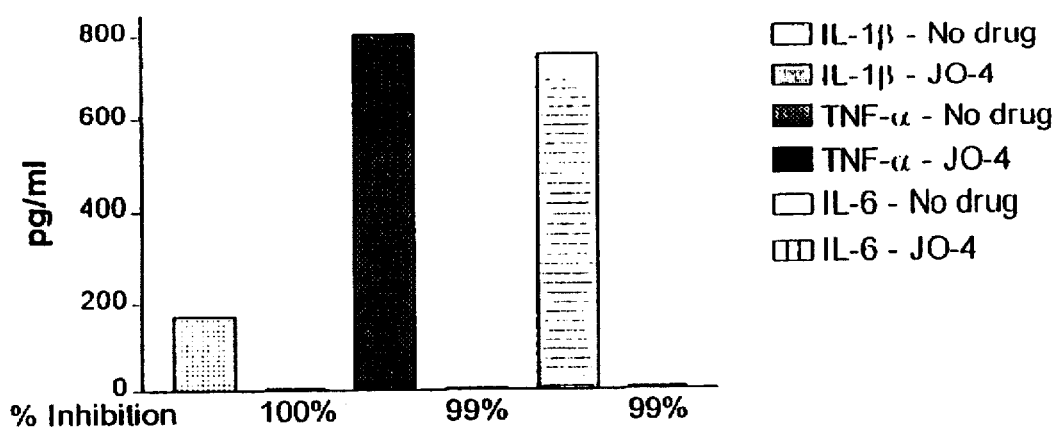
FIG. 3 shows the inhibitory effect of JO-4 on pro-inflammatory cytokine synthesis. Human PBMCs were cultured with 5 µg/ml LPS in the absence or presence of 1.0 µg/ml JO-4 in 24-well microtiter plates for 24 hours. At the end of culture, supernatants were harvested and tested by EIA for the presence of IL-1β, TNF-α, and IL-6. The results are expressed as % inhibition of control wells without drug and in pg/ml of cytokine present in the supernatant.

Inhibitory Effect of JO-4 on the induction of Pro-inflammatory cytokine synthesis Human peripheral blood mononuclear cells (PBMC) were cultured with B-cell mitogen LPS (Gibco BRL, Grand Island, N.Y.) 3 µg/mL) at $2×10^6$/mL in 1.0 mL volumes in 24-well plates in the presence of either 1 µg/mL JO-4 or medium for 48 hr. In a 37° C. incubator with 5% $CO_2$. Culture supernatants were collected at the end of incubation period and were assayed by enzyme immunoassay for the presence of the cytokines: interleukin-1β,-6 and TNF-α. Results are expressed as inhibition of cytokine production. The results are shown in FIG. 3.

Inhibitory Effect of JO-4A on human MLR

Figure 4:
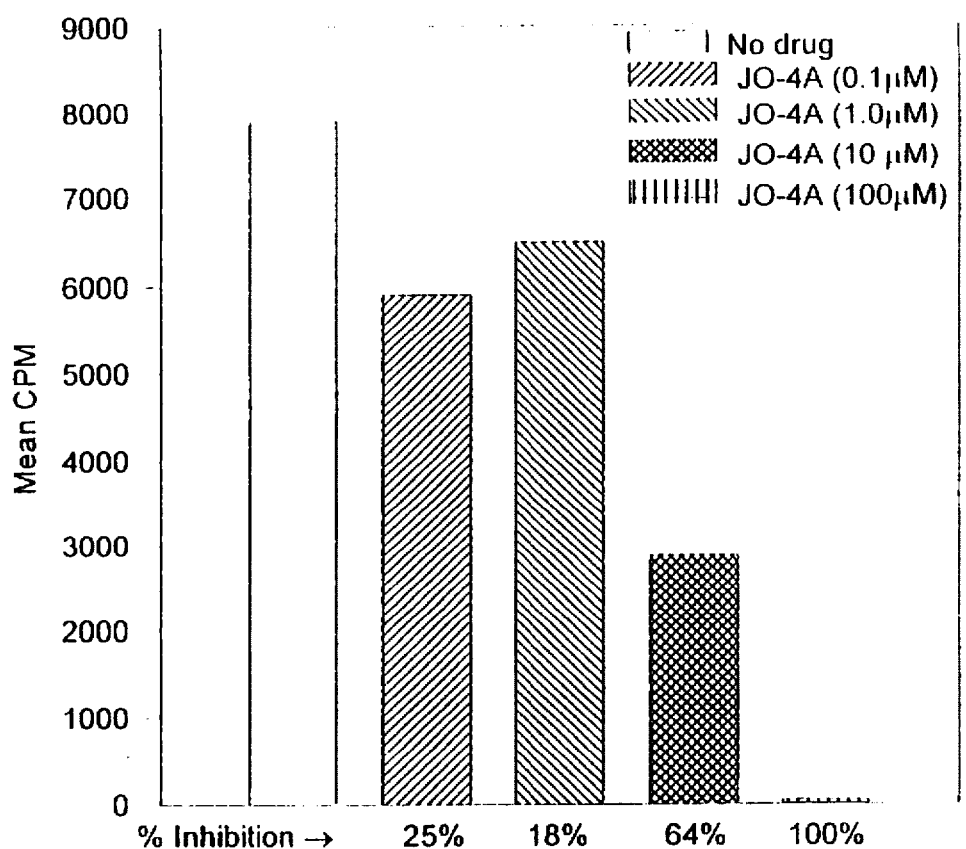
FIG. 4 shows the inhibitory effect of JO-4A on human two-way MLR. PBMCs from two individuals were co-cultured in the absnece or presence of varying concentrations of JO-4A for 5 days. Proliferation was measured by $^3$H-thymidine incorporation and expressed as mean CPM.

Two-way MLR was set up in the absence or presence of varying concentrations of JO-4A (0.1, 1.0, 10, and 100 µM). The results are depicted in FIG. 4.

Figure 5:
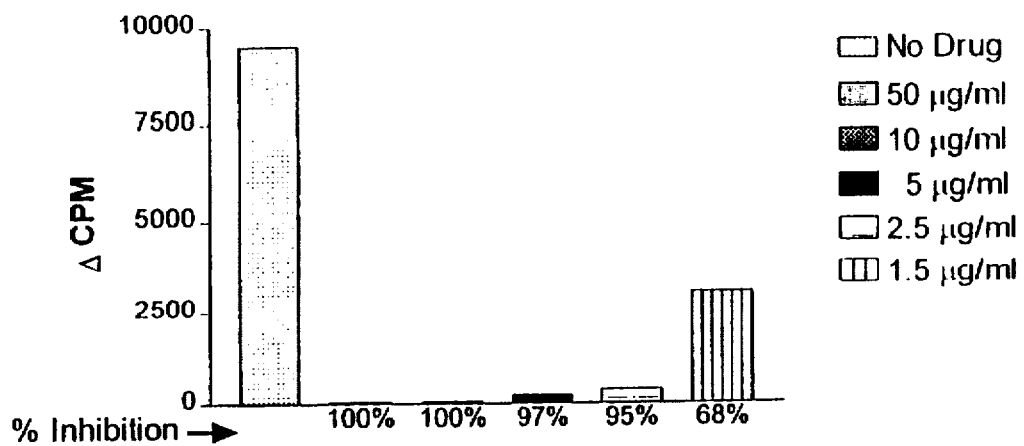
FIG. 5 shows the inhibitory effect of JO-4 on LPS-induced murine lymphocyte proliferation in vitro. Mouse spleen cells were cultured either in the absence or presence of varying concentrations of JO-4 for 48 hours with LPS (5 µg/ml). Proliferation was measured by $^3$H-thymidine incorporation and expressed as ΔCPM.

Inhibitory Effect of JO-4 on LPS-induced murine lymphocyte proliferation in vitro LPS is a B-cell mitogen in mice and it is also known to induce pro-inflammatory cytokines such as TNF-α, IL-6 and IL-1β in both murine and human mononuclear cells (Cunningham, A. J., ed; Understanding Immunology 1978;Academic Press, Inc., New York, USA). Murine lymphocytes were stimulated with LPS in vitro in the absence or presence of varying concentrations of JO-4 (1.5, 2.5, 5.0, 10.0, and 50.0 µg/mL). The results are shown in FIG. 5.

Figure 6:
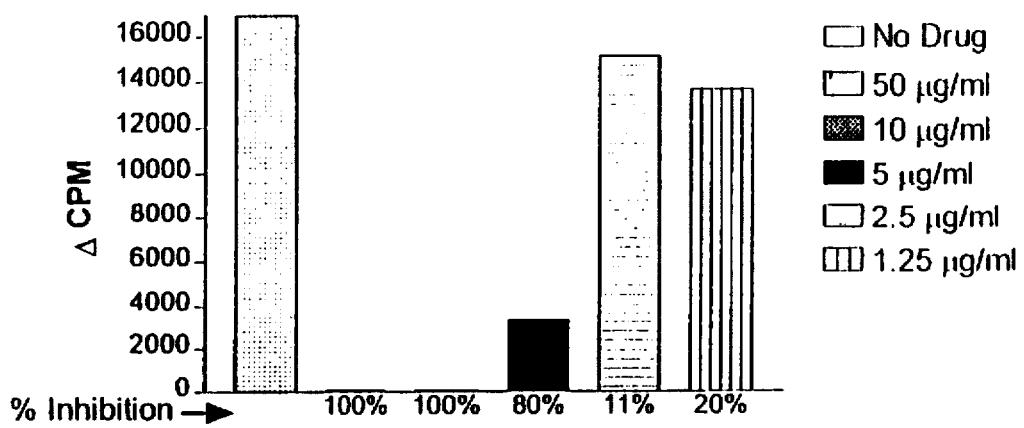
FIG. 6 shows the inhibitory effect of JO-4 on PHA-induced proliferation of human PBMCs. Human PBMCs were cultured with PHA (15 µg/ml) either in the absence or presence of varying concentrations of JO-4 for 4 days. Proliferation was measured by $^3$H-thymidine incorporation and expressed as ACPM and % inhibition of control wells without drug.

Inhibitory Effect of JO-4 on PHA-induced proliferation of human peripheral blood mononuclear cells in vitro Human PBMCs were cultured for 4 days in the absence or presence of varying concentrations of JO-4 (1.25, 2.5, 5.0, 10.0 and 50.0 µg/mL). The results are shown in FIG. 6.

PHA is a potent T-cell mitogen and stimulates T-cells to produce IL-2.

Lack of Toxicity of JO-4 on human PBMC

Figure 7:
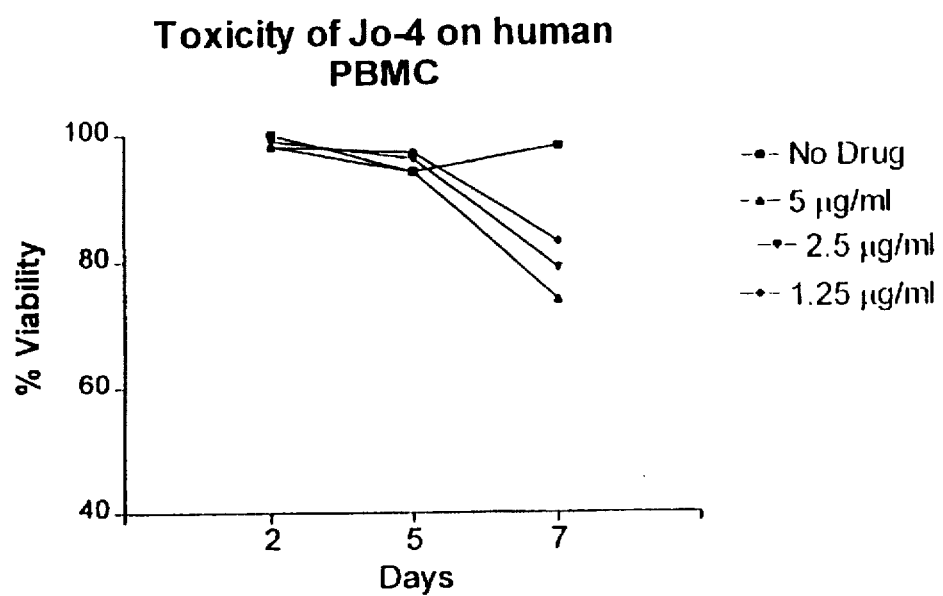
FIG. 7 shows the toxicity of JO-4 on human PBMCs. Human PBMCs were cultured either in the absence or presence of varying concentrations of JO-4. At different intervals of time, the viability was determined by trypan blue dye exclusion text and expressed as % viability of total number of cells counted.

In order to determine if JO-4 was toxic on human cells in vitro, human PBMCs were cultured in the absence or presence of varying concentrations of JO-4 (1.25, 2.5, and 5 µg/mL) for different days (2, 5 and 7 days). At the end of each incubation period, viability of cells was determined by trypan blue dye exclusion method. The results are shown in FIG. 7.

COMPOUNDS OF THE INVENTION

The compounds tested in the method of the invention included JO-4A (formula III), JO-4 (formula IV) which is an ester of JO-4A, and JO-4B (formula V).

COMPOUND PREPARATION

Preparation of JO-4A. JO-4 crystals (82 mg, 0.22 mmol) were dissolved in a mixture of methanol (3 mL) and dioxane (3 mL) with warming and then cooled to room temperature. Fresh sodium methoxide powder was added to "pH 10". The mixture was stirred at room temperature overnight and the clear, orange-yellow reaction mixture was neutralized with Dowex-50 H+ resin, filtered and evaporated in vacuo to yield a pale yellow syrup which slowly crystallized in the freezer overnight. Yield 65 mg, 90%.

Preparation of JO-4B. (Method of E. J. Corey and G. Schmidt, Tetrahedron Letters, 399–402, 1979.) JO-4A (50 mg, 0.15 mmol) was dissolved in dichloromethane (1 mL) and cooled to 0° C. and 1.5 molar equivalents of pyridinium dichromate was added with efficient stirring. The reaction mixture was allowed to stir at room temperature, for 6 hours and then diluted with ether, filtered and evaporated to yield an off-white solid (30 mg, 60%).

Esters of JO-4. As shown in formula I, the compounds of the invention comprise esters of JO-4A, but excluding hypoestoxide (JO-4), which was disclosed in Heterocycles 20:212502128 (1983) and in Z. Naturoorsch 37c:558–561 (1982). It should be noted, however, that the method of the invention for inducing immunosuppression involves administering the compounds of formula II, which includes hypoestoxide.

Accordingly, one aspect of the invention is directed to compounds of formula I

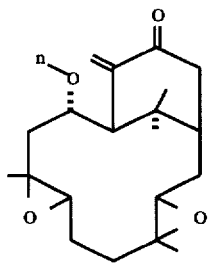

in which

R is

H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_nCOOR_2$ where n=1–4 where $R_2$ is H, an alkalai metal salt, an alkaline earth metal salt, $NH_4^+$, $N^+(R_3)_4$ where $R_3$ is independently selected from the group consisting of H and alkyl of 1 to 4 carbon atoms, $COR_1$ wherein $R_1$ is selected from the group consisting of H, $(CH_2)_nCH_3$, where n=1–6, $(CH_2)_nCOOR_2$ where n=1–4 and $R_2$ is previously defined, $(CH_2)_nN^+(R_3)_4$ wherein n=1–4, and $(CH_2)_nSO_3^-$ where N=1–4, and pharmaceutically acceptable salts thereof. A related aspect of the invention are pharmaceutical compositions comprising a therapeutically effective immunosuppressant amount of the compounds of formula 1.

The methods of the invention for inducing immunosuppression in animals which comprise administering to an animal in need of such treatment a pharamceutical composition comprising a therapeutically effective amount of the compounds of formula II

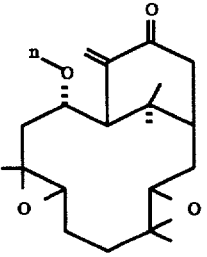

in which

R is

H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_nCOOR_2$ where n=1–4 where $R_2$ is H, an alkalai metal salt, an alkaline earth metal salt, $NH_4^+$, $N^+(R_3)_4$ where $R_3$ is independently selected from the group consisting of H and alkyl of 1 to 4 carbon atoms, $COR_1$ wherein $R_1$ is selected from the group consisting of H, $(CH_2)_nCH_3$, where n=0–6, $(CH_2)_nCOOR_2$ where n=1–4 and $R_2$ is previously defined, $(CH_2)_nN^+(R_3)_4$ wherein n=1–4, and $(CH_2)_nSO_3^-$ where N=1–4, and pharmaceutically acceptable salts thereof.

Isolation of JO-4 from *Hypoestes rosea*.

The general procedure for isolation of pure JO-4 (formula IV) from dried *Hypoestes rosea* plant material involved solid/liquid extraction using boiling hexanes in a large Soxhlet apparatus. *Hypoestes rosea* is a shrub of the family Acantheceae. (Okugun, J. I. et al., Z. Naturforsch 37c:558–561 (1982)) The crude extract obtained from the hexanes upon evaporation was subjected to flash silica gel column chromatography using a step gradient solvent system beginning with petroleum ether (30–60 bp) and stepping to 5% ethyl acetate, then to 10% and then 20%. At 30% ethyl acetate JO-4 was eluted from the column. The appropriate fractions were combined and concentrated to dryness, and petroleum ether or hexanes was added to obtain crystalline JO-4. One such procedure provided 240 mg pure JO-4 from 10 g crude extract from leaves.

Important notes: The crude extract was first dissolved in a minimum of ethyl acetate and absorbed onto silica gel and evaporated to a dry powder before loading onto the column, prepacked in petroleum ether. Extraction of specific parts of the plant indicated that the leaves were the structures that contained the majority of the JO-4 as opposed to the stems.

RESULTS

As indicated above, the compounds of formula I were found to have unexpected effectiveness as immunosuppressive and anti-inflammatory agents as shown by their effects on cellular immunity as indicated in standard in vitro and in vivo tests predictive of a compound's immunosuppressant activity in vivo in humans or other animals.

The compounds of formula I and II, in particular formulas III (JO-4A) and IV (JO-4) as demonstrated herein, immunosuppress formation of, or proliferation or function of immunocytes or lymphocytes, and are therefore useful in suppressing the rejection of transplanted tissues, e.g. organ transplants such as skin, bone marrow, kidney, heart and lung; and useful in preventing graft-versus-host disease (GVHD) and T-cell-mediated autoimmune diseases such as multiple sclerosis (MS), autoimmune thyroiditis, autoimmune myocarditis, systemic lupus erythematosus (SLD), rheumatoid arthritis (RA), Alzheimer's disease (AD), diabetes and glomerulonephritis.

Because the compounds of the invention suppressed the synthesis of pro-inflammatory cytokines (IL-1β, TNF-α, IL-6), the compounds find use for suppressing allergic reactions, asthma, contact dermatitis and skin disease such as psoriasis.

The immunosuppressant effects of the compounds of the invention were determined in the tests described above, the results of which are set forth below. It was found that the immunosuppressant medicinal activity of the claimed compounds in the in vitro and mouse in vivo tests formed the basis for the inventors' conclusions that the claimed compounds and the pharmaceutical compositions comprising them have in vivo efficacy in the inhibition of the immune system in an animal or human host.

FIG. 1 is representative of results from several experiments using different pairs of donors for each experiment. The results demonstrated that JO-4 inhibited the two-way MLR. It was concluded that the inhibitory concentration $_{50}$ ($IC_{50}$), i.e., the drug concentration capable of inducing a 50% inhibition, was between 0.5 µg/mL and 5.0 µg/mL.

FIG. 2 shows the inhibitory effect of JO-4 on MHC class I-restricted cytotoxic T lymphocyte-mediated lysis of MHC-disparate stimulator target cells. In tissue rejection reactions, it is known that MHC-restricted cytotoxic CD8+ T-cells lyse MHC-disparate donor tissue, leading to graft rejection (Abbas et al; Cellular and Molecular Immunology, 1994, W. B. Saunders Co., USA; Imagawa D. K., et al. In Aggarwal, B. B., et al; eds. Human cytokines: Their Role in Disease and Therapy, Blackwell Science, inc., Cambridge, Mass., 1995). In this experiment, it was demonstrated that JO-4 significantly (82%) inhibited the lytic capability of such cytotoxic T-cells generated from "one-way human MLR" cultures, a finding which revealed the claimed compounds' immunosuppressant activity in vitro and expectant in vivo efficacy in the inhibition of the immune system in an animal or human host.

FIG. 3 is representative of results from three experiments which demonstrated the inhibitory or immunosuppressant effect of JO-4 on pro-inflammatory cytokine synthesis (IL-1β, TNF-α and IL-6). These cytokines are known to be involved in inflammation and endotoxin-shock syndrome (Watkins et al; Pain, 1995, 63:289–302: Immune activation: the role of pro-inflammatory cytokines in inflammation, illness responses and pathological pain states).

FIG. 4 shows the inhibitory effect of JO-4A, on human two-way MLR. The $IC_{50}$ of JO-4A appeared to be between 5.0 µM and 10.0 µM. At 10.0 µM, JO-4A induced 64% inhibition of two-way MLR.

FIG. 5 shows the inhibitory effect of JO-4 on LPS-induced proliferation of murine lymphocytes in vitro. Proliferation was inhibited by more than 50% at all concentrations tested (1.5 µg/mL-50 µg/mL). Because LPS is a potent murine B lymphocyte mitogen, and B lymphocytes are the producers of plasma cells which secrete antibodies (Cunningham, A. J., ed. 1978; Academic Press, Inc;: Understanding Immunology), JO-4 and the compounds of the invention find use for preventing production of autoantibodies in autoimmune disease, such as but not restricted to systemic lupus erythromatosus, rheumatoid arthritis.

FIG. 6 shows the inhibitory effect of JO-4 on PHA-induced proliferation of human lymphocytes in vitro. PHA activation of lymphocytes leads to IL-2 production which is necessary to maintain or initiate an MLR reaction. Thus, by way of explanation but not limitation, the inhibitory effect of JO-4 on PHA-induced lymphocyte proliferation may explain its inhibitory effect on MLR.

FIG. 7 shows that JO-4 was not toxic to lymphocytes at concentrations shown to inhibit lymphocyte proliferation. Thus, the inhibitory effect of JO-4 on lymphocyte proliferation was due to its capacity to inhibit DNA synthesis without toxicity.

Figure 8:
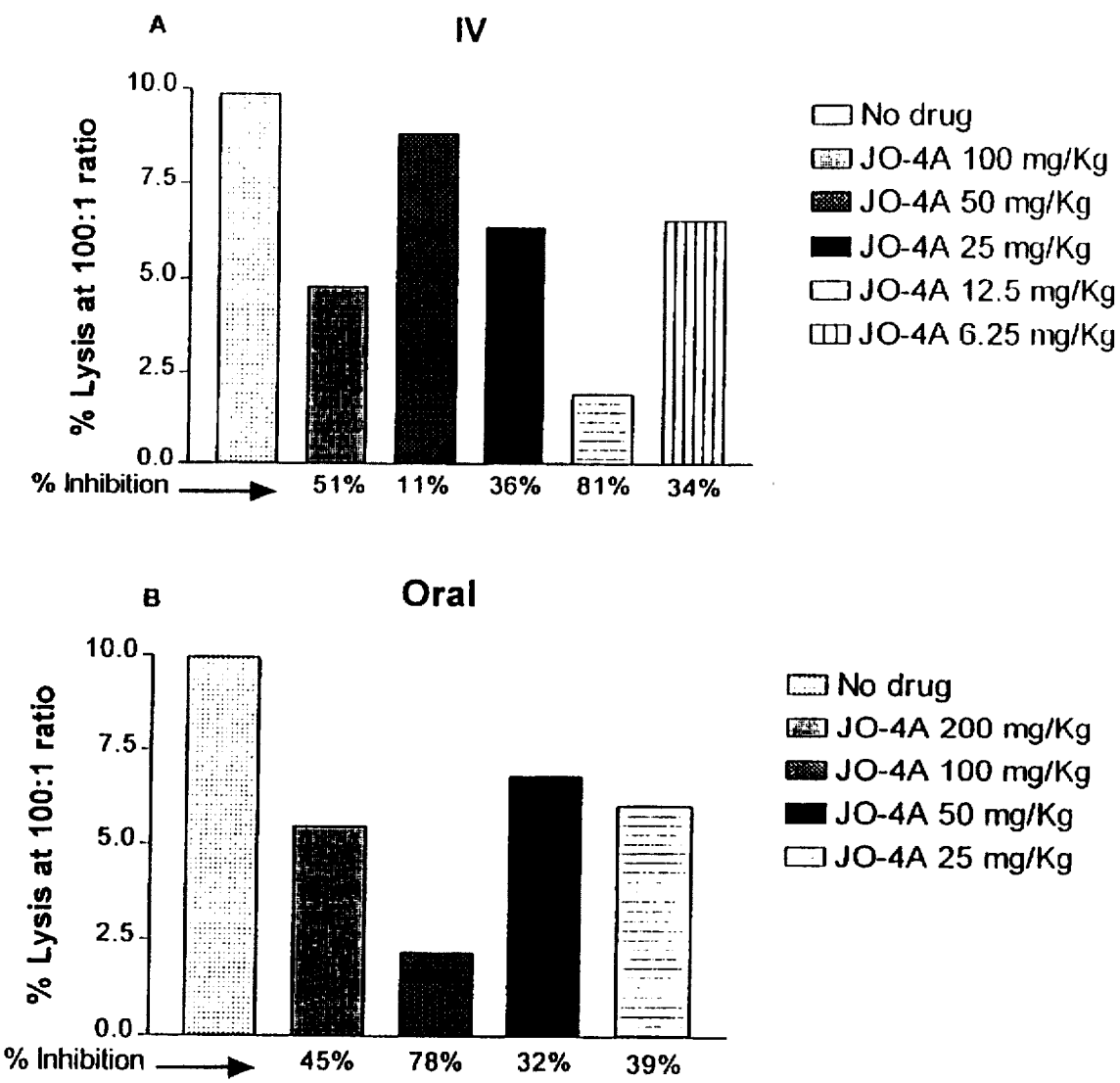
FIG. 8 shows the effects of JO-4A on NK activity in vivo. Mice were treated with varying concentrations of JO-4A either by intravenous (A) or oral (B) administration. Spleen cells were tested for NK function using YAC-1 targets in a 4-hour $^{51}$Cr-release assay.

FIG. 8 shows that JO-4A inhibited NK activity in vivo by intravenous or by oral administration. This finding demonstrated that the compounds of the invention are useful in suppressing graft-versus host disease by suppressing in vivo the activity of NK cells in the donor which are important effector cells when transplanted in systemic acute graft-versus-host disease. Accordingly, the compounds of the invention, as well as JO-4, find use in a method for preventing GVHD in a transplant recipient, which method involves administering to a transplant donor a pharmaceutical composition comprising a therapeutically effective amount of said compounds. A therapeutically effective amount of the compound is sufficient to suppress NK cell function in the donor to avoid or prevent or mitigate GVHD when the NK cells are transplanted to a recipient. It is a matter of routine skill in the art to determine optimum dosages and timing of administration of the compounds to donors in order to mitigate, avoid, or prevent GVHD in a transplant recipient.

Modifications of the modes for carrying out the invention described above that are obvious to those of skill in the chemical, biochemical, pharmaceutical and/or medical arts are intended to be within the scope of the following claims:

What is claimed is:

1. A compound having the formula

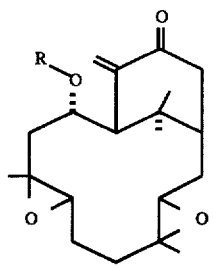

where
R is H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_n COOR_2$ where n =1–4 where $R_2$ is H, an alkalai metal salt, an alkaline earth metal salt, $NH_4^+$, $N^+(R_3)_4$ where $R_3$ is independently selected from the group consisting of H and alkyl of 1 to 4 carbon atoms, $COR_1$ wherein $R_1$ is selected from the group consisting of H, $(CH_2)_n CH_3$, where n=1–6, $(CH_2)_n COOR_2$ where n=1–4 and $R_2$ is previously defined, $(CH_2)_n N^+(R_3)_4$ wherein n=1–4, and $(CH_2)_n SO_3^-$ where N=1–4, and pharmaceutically acceptable salts thereof.

2. The compound according to claim 1 wherein R is H.

3. A pharmaceutical composition which comprises an effective immunosuppressant amount of the compound of claim 1.

4. A method for inducing immunosuppression in animals which comprises administering to an animal in need of such treatment a pharmaceutical composition comprising a therapeutically effective amount of the compound

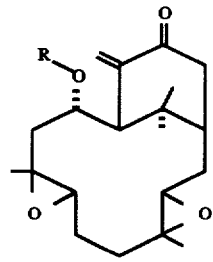

where
R is H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_n COOR_2$ where n=1–4 where $R_2$ is H, an alkalai metal salt, an alkaline earth metal salt, $NH_4^+$, $N^+(R_3)_4$ where $R_3$ is independently selected from the group consisting of H and alkyl of 1 to 4 carbon atoms, $COR_1$ wherein $R_1$ is selected from the group consisting of H, $(CH_2)_n CH_3$, where n=0–6, $(CH_2)_n COOR_2$ where n=1–4 and $R_2$ is previously defined, $(CH_2)_n N^+(R_3)_4$ wherein n=1–4, and $(CH_2)_n SO_3^-$ where N=1–4, and pharmaceutically acceptable salts thereof.

* * * * *

UNITED STATES PATENT AND TRADEMARK OFFICE
CERTIFICATE OF CORRECTION

PATENT NO : 5,801,193

DATED : September 1, 1998

INVENTOR(S) : Emmanuel A. Ojo-Amaize et al.

It is certified that error appears in the above-identified patent and that said Letters Patent is hereby corrected as shown below:

Formula I (column 1 and column 11), replace "n" with --R--.

Formula II (column 11) replace "n" with --R--.

Formula III (column 4) replace "n" with --H--.

Signed and Sealed this

Fifteenth Day of December, 1998

*Attest:*

BRUCE LEHMAN

*Attesting Officer*      Commissioner of Patents and Trademarks